(12) United States Patent
Levin et al.

(10) Patent No.: US 8,087,142 B2
(45) Date of Patent: Jan. 3, 2012

(54) PIVOTING TACKER

(75) Inventors: Shalom Levin, Atlit (IL); Nir Altman, Kibbutz Kfar Etzion (IL)

(73) Assignee: Easylap Ltd., Kfar Truman (IL)

( * ) Notice: Subject to any disclaimer, the term of this patent is extended or adjusted under 35 U.S.C. 154(b) by 802 days.

(21) Appl. No.: 12/166,329

(22) Filed: Jul. 2, 2008

(65) Prior Publication Data

US 2010/0001038 A1   Jan. 7, 2010

(51) Int. Cl.
   *B23P 11/00*   (2006.01)
   *A61B 17/04*   (2006.01)

(52) U.S. Cl. ............... 29/432; 227/175.1; 227/176.1; 227/175.2; 606/144

(58) Field of Classification Search .............. 29/432, 29/798; 606/219, 142, 143, 139, 144; 227/176.1, 227/178.1, 179.1, 901, 175.1, 175.2, 180.1, 227/73, 84, 19
See application file for complete search history.

(56) References Cited

U.S. PATENT DOCUMENTS

| | | | | |
|---|---|---|---|---|
| 4,606,343 A | * | 8/1986 | Conta et al. | 227/178.1 |
| 5,042,707 A | * | 8/1991 | Taheri | 606/213 |
| 5,258,008 A | * | 11/1993 | Wilk | 606/219 |
| 5,330,486 A | * | 7/1994 | Wilk | 606/139 |
| 5,348,259 A | * | 9/1994 | Blanco et al. | 248/276.1 |
| 5,356,064 A | * | 10/1994 | Green et al. | 227/177.1 |
| 5,564,615 A | * | 10/1996 | Bishop et al. | 227/175.1 |
| 5,779,130 A | * | 7/1998 | Alesi et al. | 227/176.1 |
| 5,810,882 A | * | 9/1998 | Bolduc et al. | 606/213 |
| 5,830,221 A | * | 11/1998 | Stein et al. | 606/157 |
| 6,280,441 B1 | * | 8/2001 | Ryan | 606/45 |
| 7,708,182 B2 | * | 5/2010 | Viola | 227/178.1 |
| 7,810,690 B2 | * | 10/2010 | Bilotti et al. | 227/175.1 |
| 7,841,503 B2 | * | 11/2010 | Sonnenschein et al. | 227/180.1 |
| 7,931,660 B2 | * | 4/2011 | Aranyi et al. | 606/143 |
| 8,006,365 B2 | * | 8/2011 | Levin et al. | 29/432 |
| 2008/0097523 A1 | * | 4/2008 | Bolduc et al. | 606/219 |
| 2010/0106167 A1 | * | 4/2010 | Boulnois et al. | 606/142 |
| 2010/0133320 A1 | * | 6/2010 | Bilotti et al. | 227/176.1 |
| 2010/0270354 A1 | * | 10/2010 | Rimer et al. | 227/175.1 |
| 2011/0079627 A1 | * | 4/2011 | Cardinale et al. | 227/176.1 |

* cited by examiner

*Primary Examiner* — Essama Omgba
(74) *Attorney, Agent, or Firm* — Dekel Patent Ltd.; David Klein (57) ABSTRACT

A tacker for applying a rotary tack, including a drive shaft coupled to a trigger, wherein operating the trigger causes rotation of the drive shaft, a magazine that holds a rotary tack rotatingly connected to the drive shaft, and an articulated applicator arm including a rotatable output shaft rotatingly connected to the magazine, wherein the magazine is proximal to the articulated applicator arm, the articulated applicator arm including one or more pivoting links, each pivoting link including a link shaft, wherein operation of the trigger causes the driver shaft and the one or more link shafts to rotate so as to distally advance the rotary tack from the magazine past the one or more pivoting links.

13 Claims, 10 Drawing Sheets

PIVOTING TACKER

FIELD OF THE INVENTION

The present invention relates generally to devices and methods for applying surgical fasteners, such as rotary tacks, to tissues, such as for hernia repairs and the like, and particularly to such devices and methods for use in laparoscopic and endoscopic procedures, wherein the tacks pass through pivoting structure.

BACKGROUND OF THE INVENTION

A number of surgical procedures require instruments that are capable of applying a surgical fastener to tissue in order to form tissue connections or to secure objects to tissue. For example, during hernia repair it is often desirable to fasten a surgical mesh to the underlying body tissue. In laparoscopic procedures, such as for hernia repair, surgery is performed in the abdomen through a small incision, while in endoscopic procedures surgery is performed through narrow endoscopic tubes inserted through small incisions in the body. Laparoscopic and endoscopic procedures generally require long and narrow instruments capable of reaching deep within the body and configured to form a seal with the incision or tube through which they are inserted.

Currently, endoscopic techniques for hernia repair utilize fasteners, such as surgical staples or clips, to secure the mesh to the tissue thereby providing reinforcement of the repair and providing structure for the encouragement of tissue ingrowth. Another type of fastener suited for use in affixing mesh to tissue, during procedures such as hernia repair, is a coil fastener having a helically coiled body portion terminating in a tissue penetrating tip, in which the helical fastener is screwed into the mesh and body tissue. An example of this type of fastener is disclosed in U.S. Pat. No. 5,258,000 to Gianturco, assigned to Cook, Inc.

U.S. patent application Ser. No. 12/022,240 to Levin and Altman, the disclosure of which is incorporated herein by reference, describes a trigger-operated mechanical tacker for applying a rotary tack. The tacker includes a drive shaft coupled to a trigger. Operating the trigger causes rotation of the drive shaft. An articulated applicator arm is pivotally connected to the drive shaft at a pivot. The articulated applicator arm includes a rotatable output shaft connected to a magazine that holds rotary tacks. The magazine is located after (distal to) the pivot. A clutch mechanism, at initial movement of the trigger, has a first orientation that causes the articulated applicator arm to pivot about the pivot until reaching a stop, and has a second orientation wherein upon continued movement of the trigger, the clutch mechanism permits the drive shaft to rotate the output shaft and cause application of the rotary tacks from the magazine.

As mentioned above, in this device the magazine is distal to the pivot. It has been found that in many applications the length of the device distal to the pivot must be quite short, which severely limits the number of tacks which the magazine can hold.

SUMMARY OF THE INVENTION

The present invention seeks to provide devices and methods for applying surgical fasteners, such as rotary tacks, to tissues, such as for hernia repairs and the like, as is described more in detail hereinbelow. In particular, the present invention seeks to provide an improvement over the device of U.S. patent application Ser. No. 12/022,240. In the instant invention, the tack magazine is proximal to the pivot and the tacks pass through pivoting structure to the distal end of the articulated applicator arm. In this manner, the tack magazine is not limited in the number of tacks it can hold.

There is thus provided in accordance with a non-limiting embodiment of the present invention a tacker for applying a rotary tack, including a drive shaft coupled to a trigger, wherein operating the trigger causes rotation of the drive shaft, a magazine that holds a rotary tack rotatingly connected to the drive shaft, and an articulated applicator arm including a rotatable output shaft rotatingly connected to the magazine, wherein the magazine is proximal to the articulated applicator arm, the articulated applicator arm including one or more pivoting links, each pivoting link including a link shaft, wherein operation of the trigger causes the driver shaft and the one or more link shafts to rotate so as to distally advance the rotary tack from the magazine past the one or more pivoting links.

In accordance with an embodiment of the present invention the magazine includes a threaded tube disposed at a distal end of the driver shaft, and the tack has coils received in threads of the threaded tube. The articulated applicator arm may include a plurality of pivoting links pivotally connected to one another in series. The pivoting links may be pivotally connected to one another or to the magazine at pinned pivot connections.

Each pivoting link may include a threaded tube. The tack advances through the one or more pivoting links by means of coils of the tack being screwed along threads of adjacent pivoting links.

In accordance with an embodiment of the present invention adjacent pivoting links pivot through an angular range before adjacent end faces of the pivoting links abut against each other to prevent further angular pivoting.

In accordance with an embodiment of the present invention threads of the threaded tube start near a pivot between the magazine and the pivoting link, and threads of the threaded tube start near a pivot between adjacent pivoting links. A thickness or pitch of the threaded tubes of the pivoting links may vary to ensure smooth advancement of the tack through the pivoting links. One or more pull cables may be disposed through the magazine and the one or more pivoting links.

There is also provided in accordance with an embodiment of the present invention a method for applying a rotary tack, including providing a drive shaft coupled to a trigger, wherein operating the trigger causes rotation of the drive shaft, a magazine that holds a rotary tack rotatingly connected to the drive shaft, and an articulated applicator arm including a rotatable output shaft rotatingly connected to the magazine, wherein the magazine is proximal to the articulated applicator arm, the articulated applicator arm including one or more pivoting links, each pivoting link including a link shaft, and operating the trigger to cause the driver shaft and the one or more link shafts to rotate so as to distally advance the rotary tack from the magazine past the one or more pivoting links.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
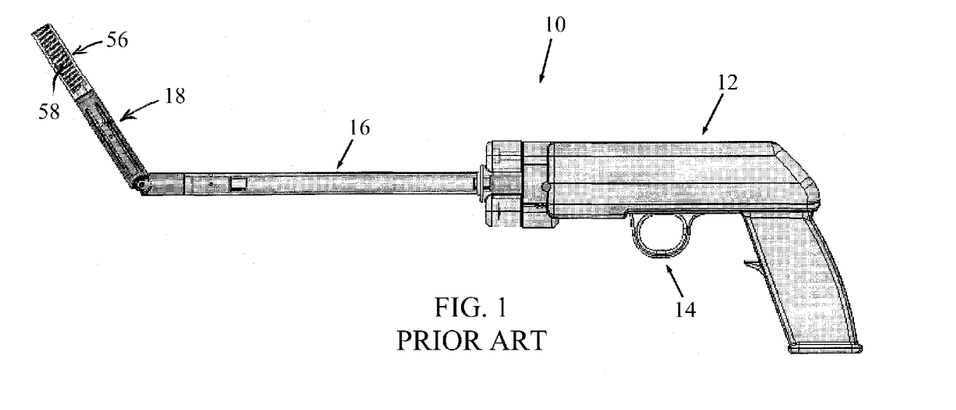
FIGS. 1 and 2 are simplified pictorial illustrations of a tacker of the prior art (U.S. patent application Ser. No. 12/022,240)
Figure 2:
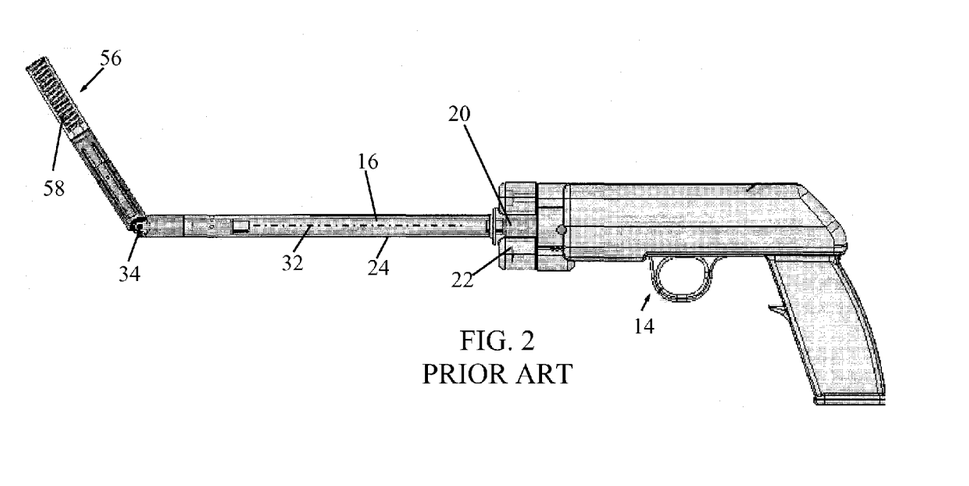
Figure 3:
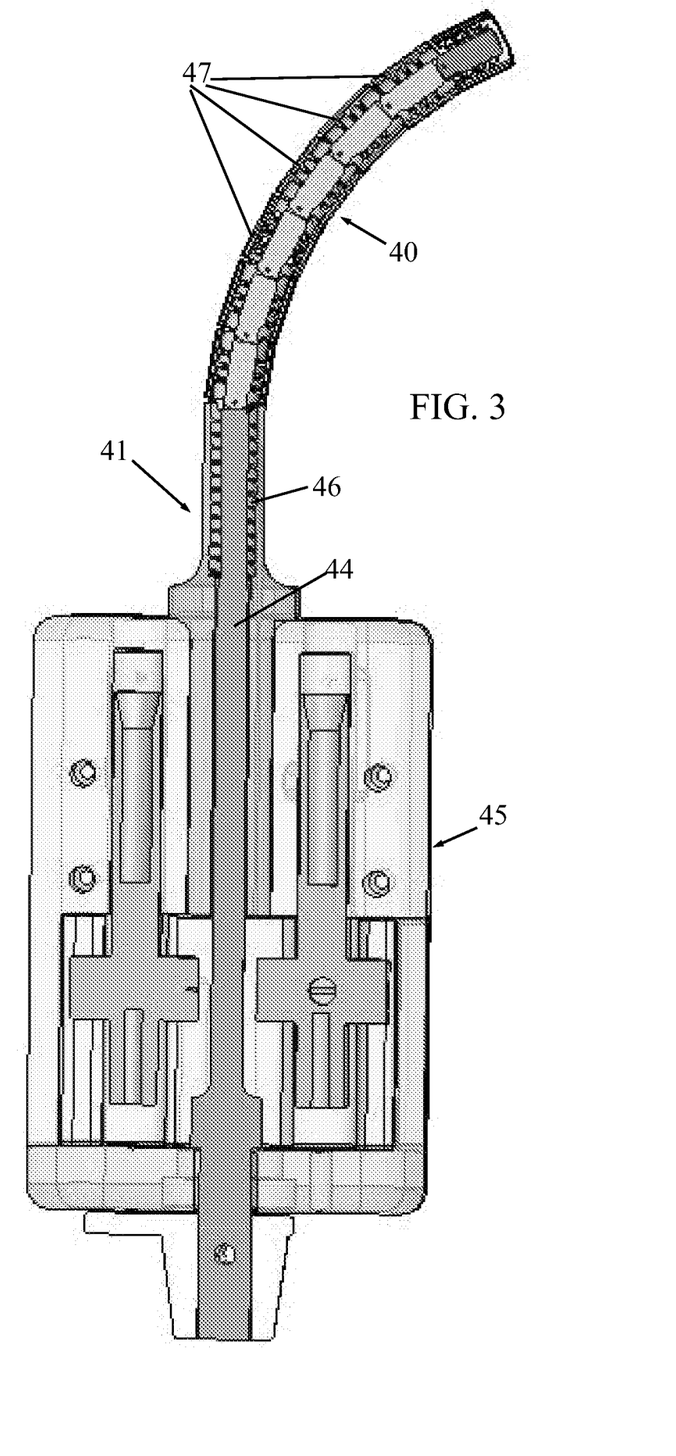
FIGS. 3-6 are pictorial illustrations of an articulated applicator arm and tack magazine, constructed and operative in accordance with an embodiment of the present invention, wherein the articulated applicator arm includes pivoting links.

Reference is now made to FIGS. 1 and 2, which illustrates a tacker 10 of the prior art (U.S. patent application Ser. No. 12/022,240).

Tacker 10 may include a handle 12 with a trigger assembly 14. A drive shaft 16 is coupled to trigger assembly 14. An articulated applicator arm 18 is pivotally connected to drive shaft 16 at a pivot 34. A magazine 56 holds rotary tacks 58 and is positioned distal to pivot 34 (FIG. 2).

A proximal end 20 (FIG. 2) of drive shaft 16 is splined (or otherwise suitably shaped) for mating with a drive assembly (not shown) of trigger assembly 14. The proximal end 20 of drive shaft 16 is journaled in a roller bearing housing 22 (FIG. 2). Drive shaft 16 extends through an extension tube (also called housing) 24. Upon operation of trigger assembly 14, the drive assembly turns drive shaft 16 about a longitudinal axis 32 thereof (FIG. 2), and causes deployment of tack 58 from magazine 56.

Reference is now made to FIGS. 3-6, which illustrate an articulated applicator arm 40 and tack magazine 41, constructed and operative in accordance with an embodiment of the present invention. The articulated applicator arm 40 and tack magazine 41 may be used with tacker 10 by replacing the articulated applicator arm and tack magazine of the prior art. Unlike the prior art, tack magazine 41 is proximal to articulated applicator arm 40, as is now described.

Tack magazine 41 holds rotary tacks 42. Magazine 41 includes a housing 43 in which a drive shaft 44 is journaled. Drive shaft 44 is connected at a proximal end thereof with a drive assembly 45, which connects to trigger assembly 14 (for example, as described in U.S. patent application Ser. No. 12/022,240. Upon operation of the trigger assembly 14, the drive assembly 45 turns drive shaft 44 about its longitudinal axis (similar to U.S. patent application Ser. No. 12/022,240).

Tack magazine 41 includes a threaded tube 46 disposed at a distal end of driver shaft 44. Tacks 42 are stored in magazine 41 with the coils of tacks 42 being received in the threads of threaded tube 46. Any number of tacks 42 can be stored in magazine 41, such as a dozen or more.

Articulated applicator arm 40 includes pivoting links 47 pivotally connected to one another in series. As seen best in FIG. 4, a housing 52 of each pivoting link 47 includes a link shaft 48 with proximal and distal pivot connections (e.g., pinned connections). For example, the pivoting link 47 closest to tack magazine 41 is pivotally connected to magazine 41 at a pivot connection 49. The next most distal pivoting link 47 is pivotally connected to the previous pivoting link 47 at a pivot connection 50. By means of the pinned connection, when driver shaft 44 turns all the pivoting links 47 turn as well about their respective longitudinal axes.

Figure 4:
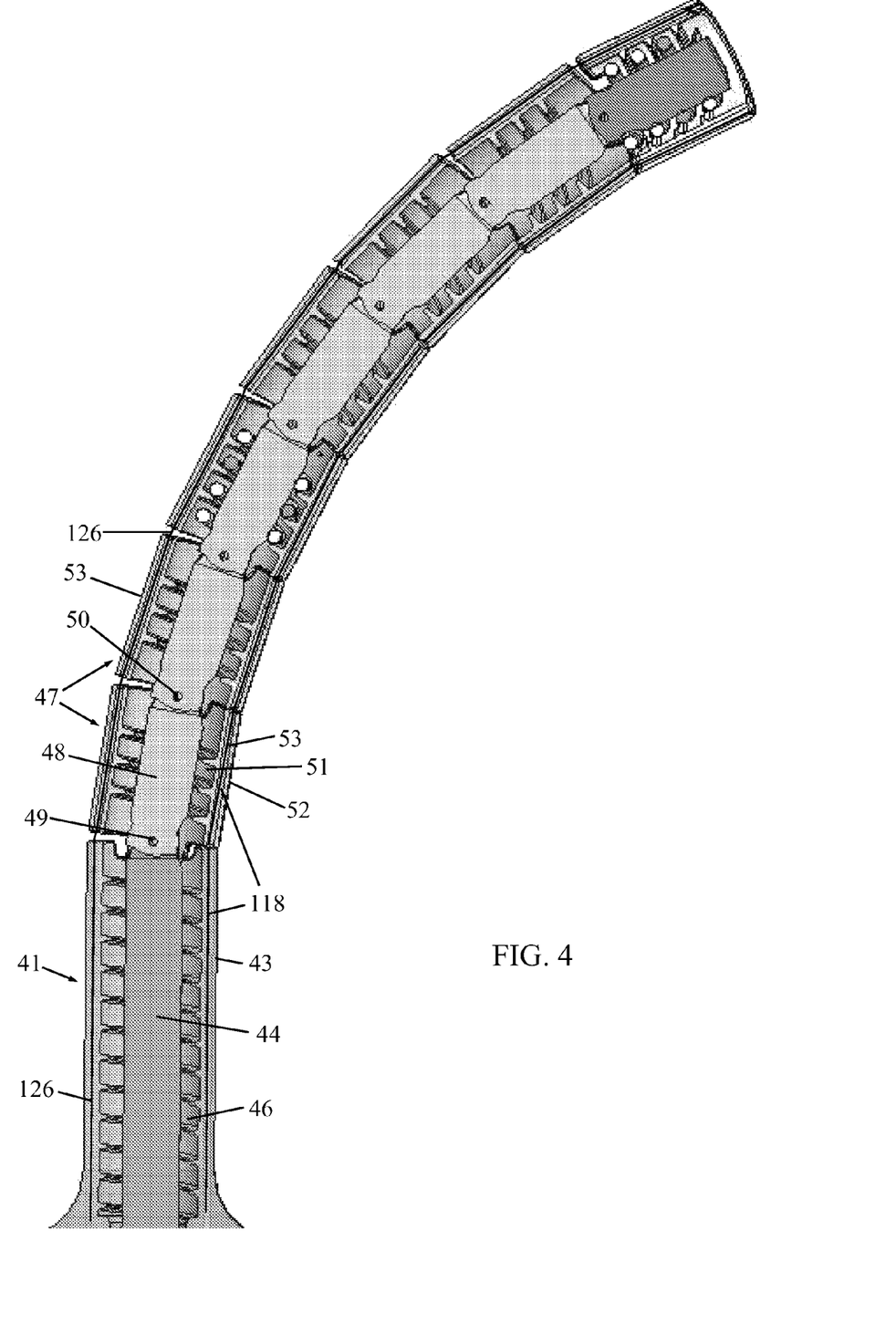
Figure 4A:
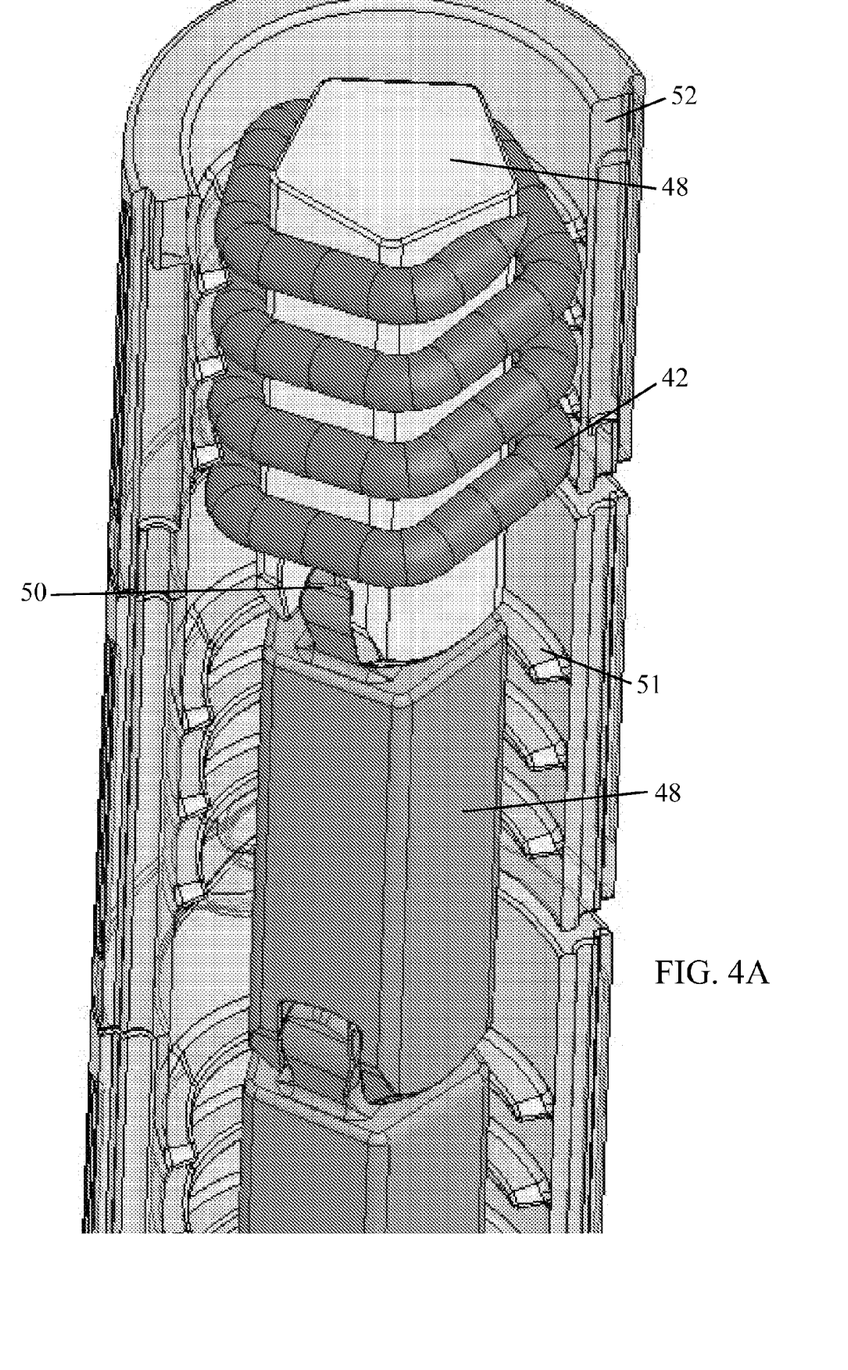
Figure 5:
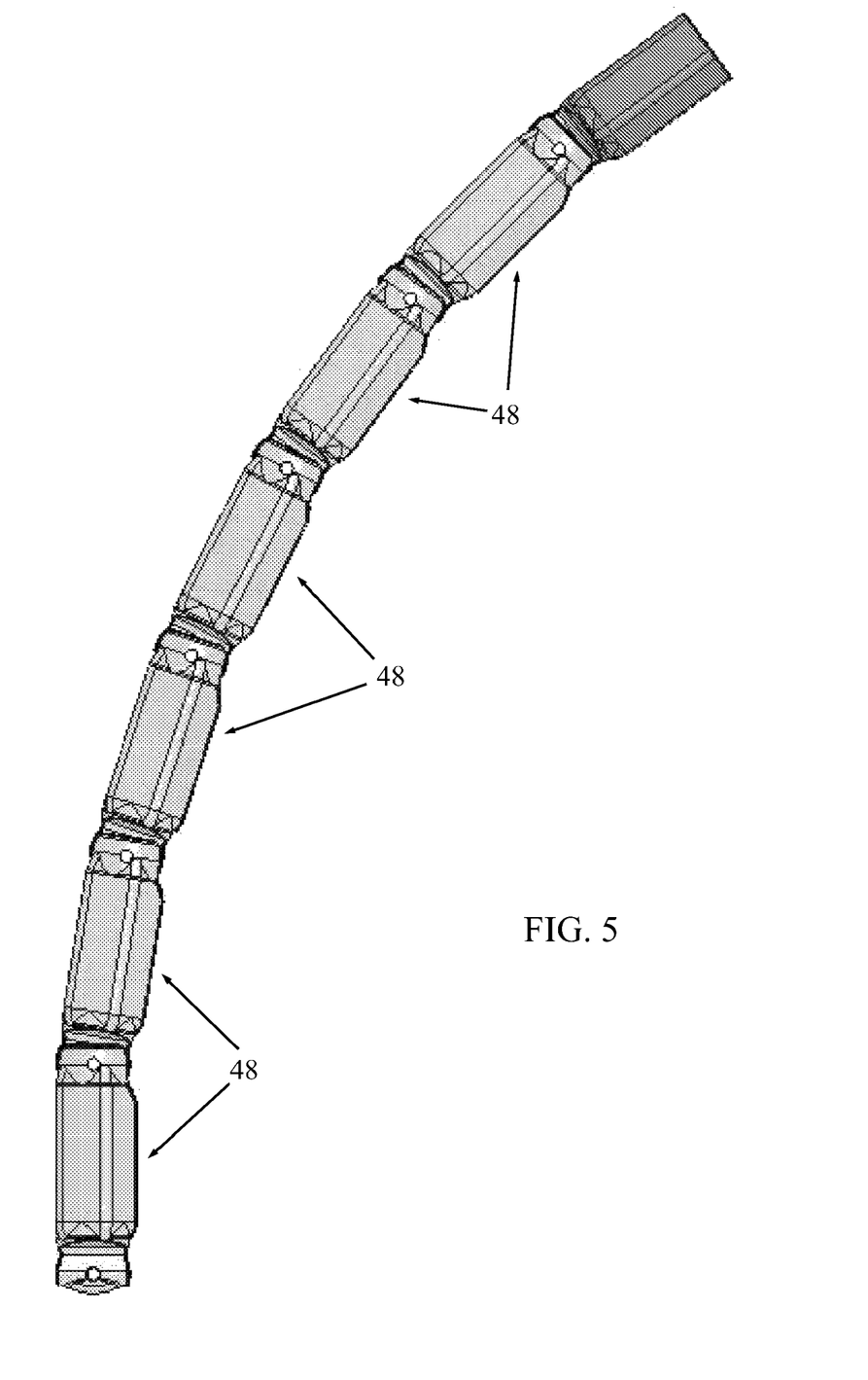

Each pivoting link 47 includes a threaded tube 51, similar to threaded tube 46, and tacks 42 advance through the pivoting links 47 by means of the coils of tacks 42 being screwed along the threads of adjacent pivoting links 47. The adjacent pivoting links 47 can pivot through an angular range before their adjacent end faces abut against each other to prevent further angular pivoting. For example, the relative maximum pivoting angle between two adjacent pivoting links 47 is preferably in the range of 5-15°. For example, by using six adjacent pivoting links 47 with a maximum pivoting angle of 10°, the total pivoting angle for articulated applicator arm 40 is 60°.

Figure 6:
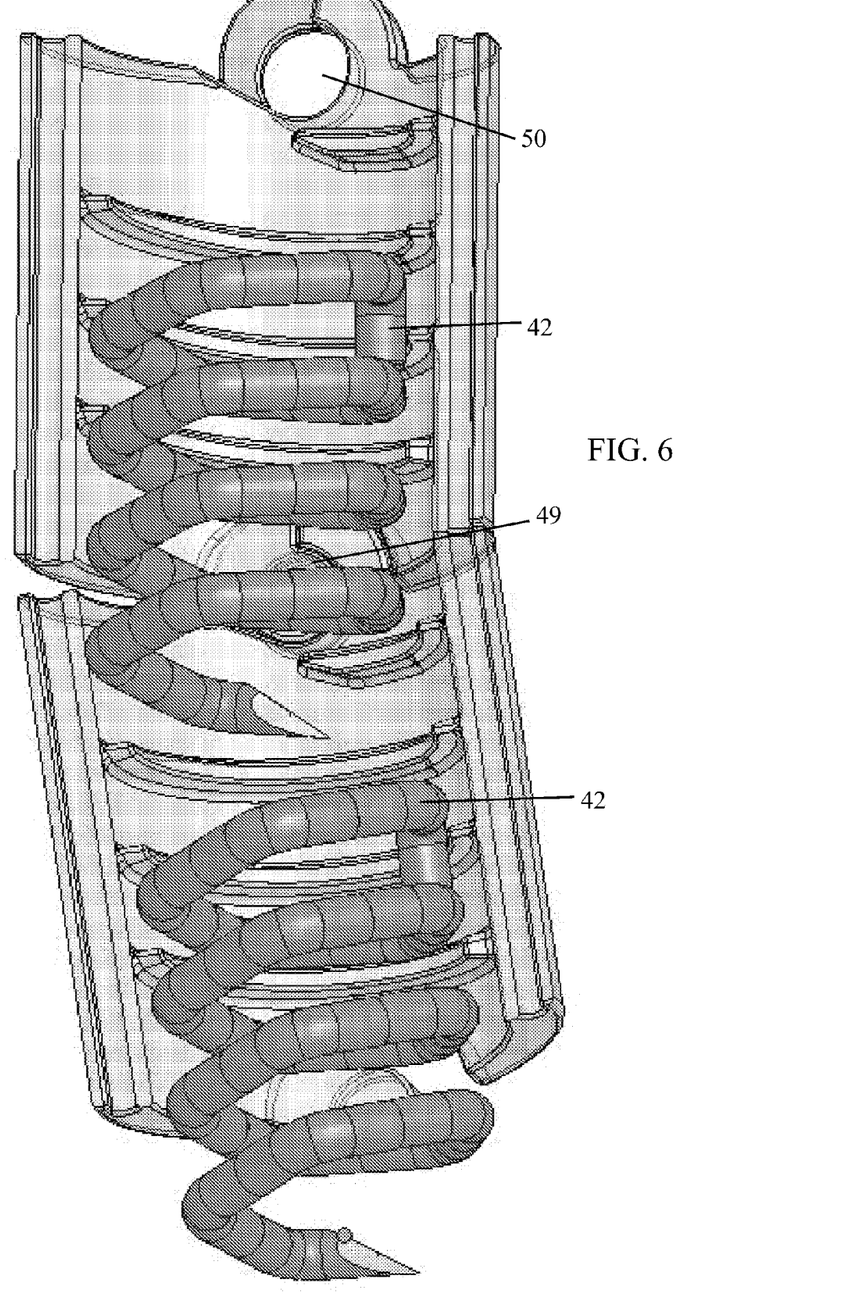

As seen particularly in FIG. 6, the starting point of the threaded tube 46/51 is preferably near or a little bit above the pivot 49/50 to ensure smooth and correct engagement of the tip of the tack 42 when entering the next adjacent link 47. In addition, to compensate for the bending of the links 47, the thickness of the threads or the pitch of the threads in the threaded tube 46/51 may vary to ensure smooth advancement of the tacks 42.

Referring again to FIG. 4, the housing 52 of each pivoting link 47 and the housing 43 of magazine 41 may be formed with a pair of diametrically opposing bores 53 in which pull cables 118 and 126 are disposed. As similarly described in U.S. patent application Ser. No. 12/022,240, pull cables 118 and 126 are attached to the trigger assembly 14 and are used to manipulate articulated applicator arm 40.

Figure 9:
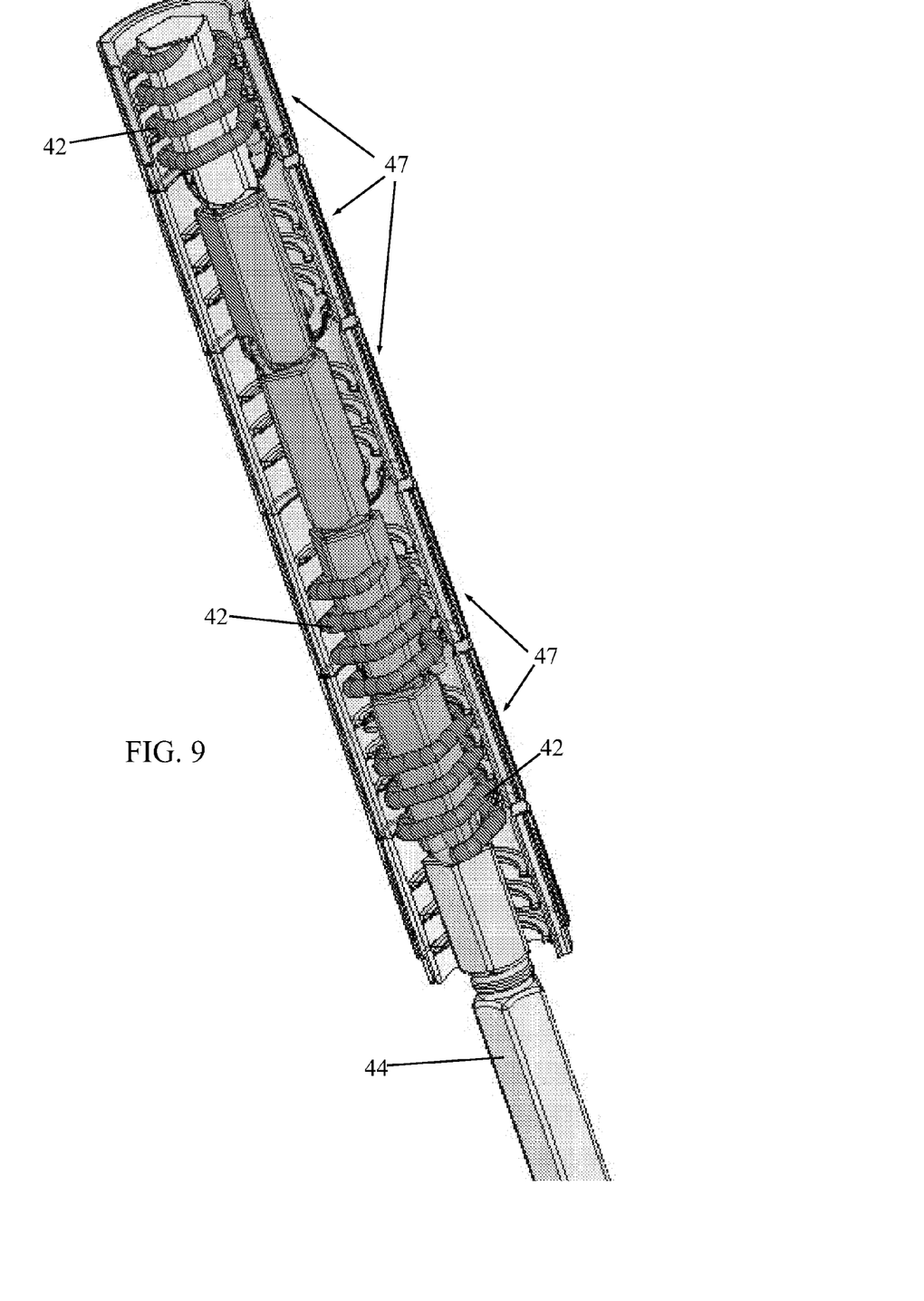
FIG. 9 is a simplified pictorial illustration of the articulated applicator arm at a straight angle.

In operation, the user pulls a trigger or other actuating device to cause driver shaft 44 and all the pivoting links 47 to rotate. This distally advances the tacks 42, one-by-one, from magazine 41 through and past each pivoting link 47 until the tack 42 is advanced off the most distal pivoting link 47 and screws into tissue (not shown). The pull cables 118 and 126 are manipulated by the operator of trigger assembly 14 to pivot articulated applicator arm 40 to any desired angle. Articulated applicator arm 40 can thus be used at a variety of angles, even a straight orientation as shown in FIG. 9.

Figure 7:
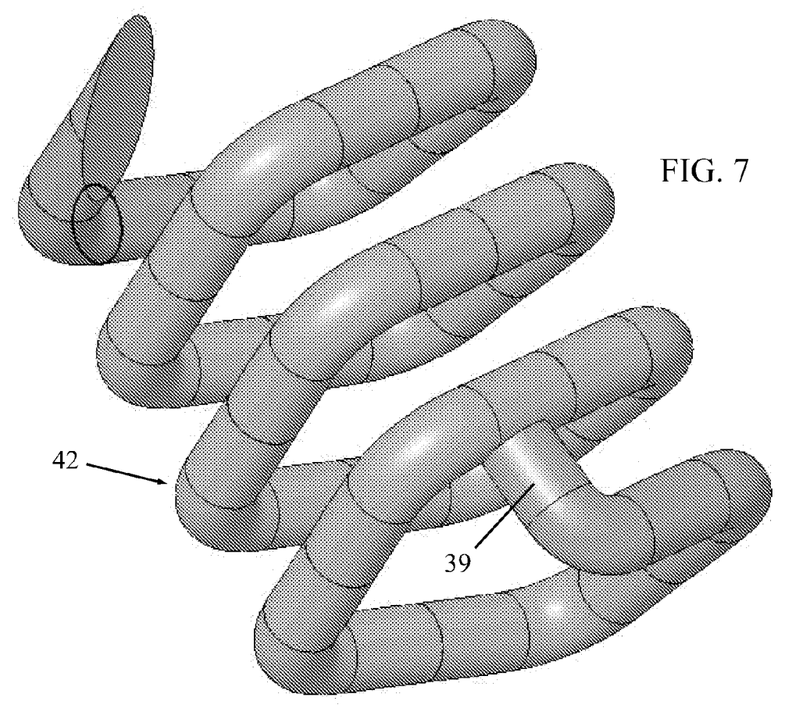
FIG. 7 is a simplified pictorial illustration of a square tack with a closed end, constructed and operative in accordance with an embodiment of the present invention.
Figure 8:
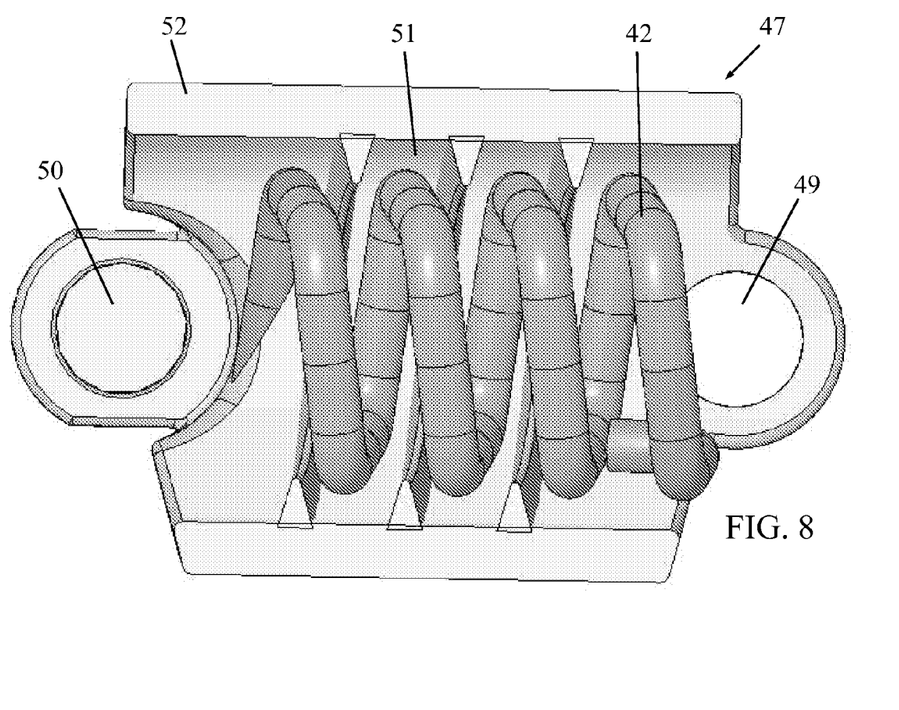
FIG. 8 is a simplified pictorial illustration of a pivoting link of the articulated applicator arm, constructed and operative in accordance with an embodiment of the present invention.
Figure 10:
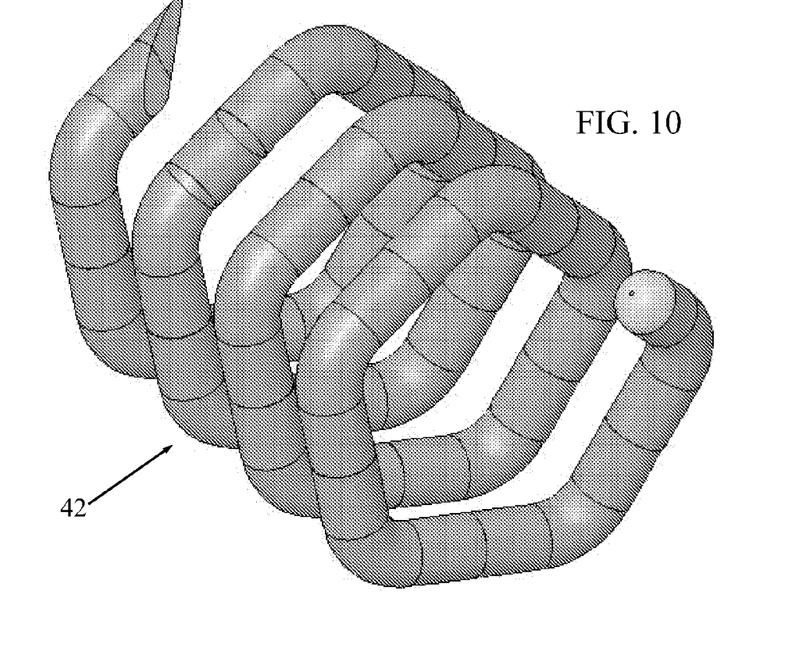
FIG. 10 is a simplified pictorial illustration of a pentagonal tack, constructed and operative in accordance with an embodiment of the present invention.
Figure 11:
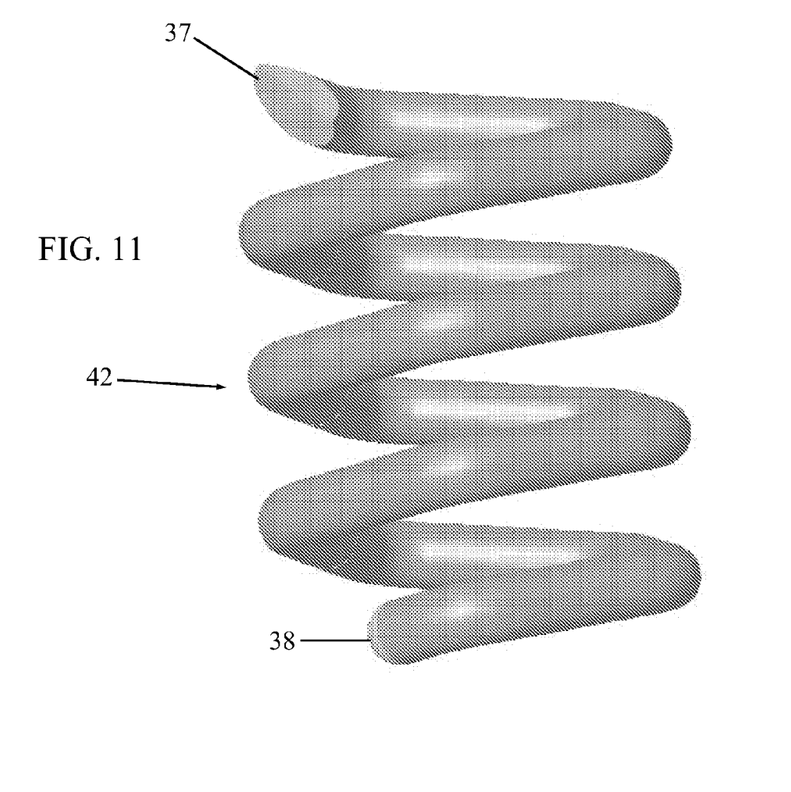
FIG. 11 is a simplified pictorial illustration of a circular tack, constructed and operative in accordance with an embodiment of the present invention.
Figure 12:
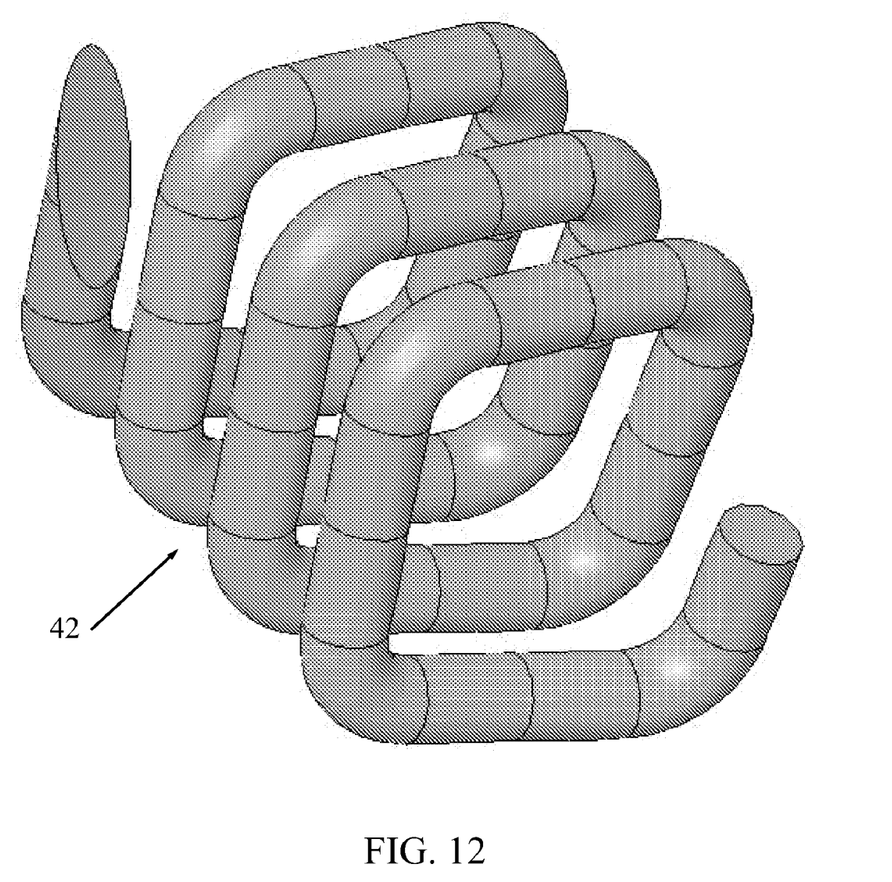
FIG. 12 is a simplified pictorial illustration of a square tack, constructed and operative in accordance with another embodiment of the present invention.

The tack 42 may have a variety of shapes, such as circular (FIG. 11, showing a dual sharpened edge 37 and a round edge 38), square or rectangular (FIGS. 7 and 12, with the one in FIG. 7 having a closed end 39), pentagonal (FIG. 10) or other non-circular, polygonal or non-polygonal shapes and combinations thereof. The inner portion of articulated applicator arm 40 that accommodates the tacks (e.g., threaded tubes 46/51 of tack magazine 41, pivoting links 47 and drive shaft 44) may be correspondingly shaped to match the shape of tacks 41 (e.g., circular, non-circular, polygonal or non-polygonal shapes and combinations thereof).

In another embodiment, instead of pivoting links, articulated applicator arm 40 (or portions thereof, such as link shaft 48) may be constructed of a flexible material or may be constructed to be flexible and bendable (such as like a mesh).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A tacker for applying a rotary tack, comprising:
   a drive shaft coupled to a trigger, wherein operating said trigger causes rotation of said drive shaft;
   a magazine that holds a rotary tack rotatingly connected to said drive shaft; and
   an articulated applicator arm comprising a rotatable output shaft rotatingly connected to said magazine, wherein said magazine is proximal to said articulated applicator arm, said articulated applicator arm comprising one or more pivoting links, each pivoting link comprising a link shaft, wherein operation of said trigger causes said drive shaft and said one or more link shafts to rotate so as to distally advance said rotary tack from said magazine past said one or more pivoting links.

2. The tacker according to claim 1, wherein said magazine comprises a threaded tube disposed at a distal end of said drive shaft, and wherein said tack has coils received in threads of said threaded tube.

3. The tacker according to claim 2, wherein threads of said magazine threaded tube start near a pivot between said magazine and said pivoting link.

4. The tacker according to claim 1, wherein said articulated applicator arm comprises a plurality of pivoting links pivotally connected to one another in series.

5. The tacker according to claim 1, wherein said one or more pivoting links are pivotally connected to one another or to said magazine at pinned pivot connections.

6. The tacker according to claim 5, wherein adjacent pivoting links pivot through an angular range before adjacent end faces of said pivoting links abut against each other to prevent further angular pivoting.

7. The tacker according to claim 1, wherein each pivoting link comprises a threaded tube, and said tack advances through the one or more pivoting links by means of coils of said tack being screwed along threads of adjacent pivoting links.

8. The tacker according to claim 7, wherein threads of each said pivoting link threaded tube start near a pivot between adjacent pivoting links.

9. The tacker according to claim 7, wherein a thickness or pitch of said threaded tubes of said pivoting links vary to ensure smooth advancement of said tack through said pivoting links.

10. The tacker according to claim 1, wherein one or more pull cables are disposed through said magazine and said one or more pivoting links.

11. The tacker according to claim 1, wherein said tack has a non-circular shape.

12. The tacker according to claim 11, wherein an inner portion of said articulated applicator arm that accommodates said tack has a non-circular shape correspondingly shaped to match the shape of said tack.

13. A method for applying a rotary tack, comprising:
    providing a drive shaft coupled to a trigger, wherein operating said trigger causes rotation of said drive shaft, a magazine that holds a rotary tack rotatingly connected to said drive shaft, and an articulated applicator arm comprising a rotatable output shaft rotatingly connected to said magazine, wherein said magazine is proximal to said articulated applicator arm, said articulated applicator arm comprising one or more pivoting links, each pivoting link comprising a link shaft; and
    operating said trigger to cause said drive shaft and said one or more link shafts to rotate so as to distally advance said rotary tack from said magazine past said one or more pivoting links.

* * * * *